(12) United States Patent
Lee et al.

(10) Patent No.: US 10,800,825 B2
(45) Date of Patent: Oct. 13, 2020

(54) IL-21 (HETERODIMERIC FC-FUSED IL-21) FUSED TO IMMUNOGLOBULIN HEAVY CHAIN CONSTANT REGION HETERODIMER (HETERODIMERIC FC), AND PHARMACEUTICAL COMPOSITION COMPRISING SAME

(71) Applicants: Korea University Research and Business Foundation, Seoul (KR); AJOU UNIVERSITY INDUSTRY-ACADEMIC COOPERATION FOUNDATION, Suwon-si, Gyeonggi-do (KR)

(72) Inventors: Kyung-Mi Lee, Seoul (KR); Seon Ah Lim, Seoul (KR); Yong Sung Kim, Suwon-si (KR); Ye Jin Kim, Busan (KR)

(73) Assignees: Korea University Research and Business Foundation, Seoul (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/329,817

(22) PCT Filed: Aug. 31, 2017

(86) PCT No.: PCT/KR2017/009570
§ 371 (c)(1),
(2) Date: Mar. 1, 2019

(87) PCT Pub. No.: WO2018/044105
PCT Pub. Date: Mar. 8, 2018

(65) Prior Publication Data
US 2019/0218267 A1    Jul. 18, 2019

(30) Foreign Application Priority Data

Sep. 2, 2016 (KR) .......................... 10-2016-0113452

(51) Int. Cl.
| | |
|---|---|
| *C07K 14/54* | (2006.01) |
| *A61K 38/20* | (2006.01) |
| *A61K 45/06* | (2006.01) |
| *A61K 47/68* | (2017.01) |
| *A61P 35/00* | (2006.01) |
| *A61K 35/17* | (2015.01) |

(52) U.S. Cl.
CPC .............. *C07K 14/54* (2013.01); *A61K 35/17* (2013.01); *A61K 38/20* (2013.01); *A61K 38/2013* (2013.01); *A61K 45/06* (2013.01); *A61K 47/68* (2017.08); *A61P 35/00* (2018.01); *C07K 2317/526* (2013.01); *C07K 2317/53* (2013.01); *C07K 2317/71* (2013.01); *C07K 2319/30* (2013.01)

(58) Field of Classification Search
CPC ...................................................... C07K 14/54
See application file for complete search history.

(56) References Cited

U.S. PATENT DOCUMENTS

| 7,695,936 B2 | 4/2010 | Carter et al. |
| 2015/0094451 A1 | 4/2015 | Fischer et al. |

FOREIGN PATENT DOCUMENTS

| JP | 2015-522525 A | 8/2015 |
| JP | 2016-514161 A | 5/2016 |
| KR | 10-2014-0067944 A | 6/2014 |
| KR | 10-1522954 B1 | 5/2015 |
| KR | 10-2015-0130342 A | 11/2015 |
| KR | 10-1643165 B1 | 7/2016 |
| WO | 03/087320 A2 | 10/2003 |
| WO | 2013/166594 A1 | 11/2013 |
| WO | 2013/169693 A1 | 11/2013 |
| WO | 2014/084607 A1 | 6/2014 |

OTHER PUBLICATIONS

Choi, Hye-Ji et al., "Engineering of Immunoglobulin Fc Heterodimers Using Yeast Surface-Displayed Combinatorial Fc Library Screening", PLOS ONE, Dec. 16, 2015, vol. 10, No. 12, e0145349, pp. 1-20 (total 20 pages).
Ha, Ji-Hee et al., "Immunoglobulin Fc Heterodimer Platform Technology: From Design to Applications in Therapeutic Antibodies and Proteins", Frontiers in Immunology, Oct. 2016, vol. 7, Article 394, pp. 1-16 (total 16 pages).
Spreter Von Kreudenstein, Thomas et al., "Protein engineering and the use of molecular modeling and simulation: The case of heterodimeric Fc engineering", Methods, 2014, vol. 65, pp. 77-94 (total 18 pages).
Ridgway et al., "'Knobs-into-holes' engineering of antibody $C_H3$ domains for heavy chain heterodimerization", Protein Engineering, 1996, vol. 9, No. 7, pp. 617-621 (total 5 pages).
Von Kreudenstein et al., "Improving biophysical properties of a bispecific antibody scaffold to aid developability", mAbs, Oct. 2013, vol. 5, Issue 5, pp. 646-654 (total 9 pages).

(Continued)

*Primary Examiner* — Prema M Mertz
(74) *Attorney, Agent, or Firm* — Sughrue Mion, PLLC

(57) ABSTRACT

A heterodimeric Fc-fused protein and a pharmaceutical composition comprising the heterodimeric Fc-fused protein are disclosed. The heterodimeric Fc-fused protein comprises first and second Fc regions of an immunoglobulin heavy chain constant region (Fc) pair and in which IL-21 is bound to at least one of the N-terminus or the C-terminus of the first Fc region and/or the second Fc region, wherein CH3 domains of the first Fc region and the second Fc region are mutated such that the formation of a heterodimer is promoted.
When the heterodimeric Fc-fused protein according to the present invention is used, an in vivo half-life of IL-21 included in the heterodimeric Fc-fused protein may be significantly increased.

6 Claims, 11 Drawing Sheets

Specification includes a Sequence Listing.

(56) References Cited

OTHER PUBLICATIONS

Moore et al., "A novel bispecific antibody format enables simultaneous bivalent and monovalent co-engagement of distinct target antigens", mAbs, 2011, vol. 3, Issue 6, pp. 546-557 (total 12 pages).
Davis et al., "SEEDbodies: fusion proteins based on strand-exchange engineered domain (SEED) $C_H3$ heterodimers in an Fc analogue platform for asymmetric binders or immunofusions and bispecific antibodies", Protein Engineering, Design & Selection, 2010, vol. 23, No. 4, pp. 195-202 (total 8 pages).
Choi et al., "A Heterodimeric Fc-Based Bispecific Antibody Simultaneously Targeting VEGFR-2 and Met Exhibits Potent Antitumor Activity", Molecular Cancer Therapeutics, Dec. 2013, vol. 12, No. 12, pp. 2748-2759 (total 13 pages).
Irani et al., "Molecular properties of human IgG subclasses and their implications for designing therapeutic monoclonal antibodies against infectious diseases", Molecular Immunology, 2015, vol. 67, pp. 171-182 (total 12 pages).
Cesana et al., "Characterization of $CD4^+CD25^+$ Regulatory T Cells in Patients Treated With High-Dose Interleukin-2 for Metastatic Melanoma or Renal Cell Carcinoma", Journal of Clinical Oncology, Mar. 1, 2006, vol. 24, No. 7, pp. 1169-1177 (total 9 pages).
Wei et al., "Interleukin-2 Administration Alters the $CD4^+FOXP3^+$ T-Cell Pool and Tumor Trafficking in Patients with Ovarian Carcinoma", Cancer Research, Aug. 1, 2007, vol. 67, No. 15, pp. 7487-7494 (total 9 pages).
Al-Chami et al., "Therapeutic utility of the newly discovered properties of interleukin-21", Cytokine, 2016, vol. 82, pp. 33-37 (total 5 pages).
Parrish-Novak et al., "Interleukin 21 and its receptor are involved in NK cell expansion and regulation of lymphocyte function", Nature, Nov. 2, 2000, vol. 408, pp. 57-63 (total 7 pages).
Denman et al., "Membrane-Bound IL-21 Promotes Sustained Ex Vivo Proliferation of Human Natural Killer Cells", PLOS ONE, Jan. 2012, vol. 7, Issue 1, e30264, pp. 1-13 (total 13 pages).
Shin et al., "Ex vivo expansion of canine cytotoxic large granular lymphocytes exhibiting characteristics of natural killer cells", Veterinary Immunology and Immunopathology, 2013, vol. 153, pp. 249-259 (total 11 pages).
Zhu et al., "Identification of cereblon-binding proteins and relationship with response and survival after IMiDs in multiple myeloma", Blood, Jul. 24, 2014, vol. 124, No. 4, pp. 536-545 (total 11 pages).
Gillies et al., "Improving the Efficacy of Antibody-Interleukin 2 Fusion Proteins by Reducing Their Interaction with Fc Receptors", Cancer Research, May 1, 1999, vol. 59, pp. 2159-2166 (total 9 pages).
Yan et al., "How can we improve antibody-based cancer therapy?", mAbs, 2009, vol. 1, No. 1, pp. 67-70 (total 5 pages).
Korean Intellectual Property Office; Communication dated Dec. 4, 2018 issued in counterpart application No. 10-2016-0113452.
Korean Intellectual Property Office; Communication dated Apr. 18, 2018 issued in counterpart application No. 10-2016-0113452.
International Search Report for PCT/KR2017/009570 dated Dec. 8, 2017 [PCT/ISA/210].
Moroz et al., "IL-21 Enhances and Sustains $CD8^+$ Cell Responses to Achieve Durable Tumor Immunity: Comparative Evaluation of IL2, IL-15, and IL-21[1]", The Journal of Immunology, 2004, vo. 173, pp. 900-909, 11 pages total.
Choi et al., "Crystal structures of immunoglobulin Fc heterodimers reveal the molecular basis for heterodimer formation", Molecular Immunology, vol. 65 (2015) pp. 377-383, 7 pages total.
"Antibody drug / Fc fusion protein", National Institute of Health Sciences, Division of Biological Chemistry and Biologicals, National-Institute-of-Health-Sciences organism medicine part, Aug. 26, 2016 [online, retrieved on Feb. 14, 2020] URL: https://web.archive.org/web/20160826132302/http://www.nihs.go.jp/dbcb/mabs.html, 5 pages total.
Pallikkuth et al., "Recombinant IL-21 induces perforin and granzyme B in total and virus specific CD8 Tcells in acute and early stages of SIV infection in rhesus macaques", Retrovirology, 2012, vol. 9 (Suppl. 2), p. 13, doi:10.1186/1742-4690-9-S2-P13, 1 page total.
Pallikkuth et al., "Maintenance of Intestinal Th17 Cells and Reduced Microbial Translocation in SIV-infected Rhesus Macaques Treated with Interleukin (IL)-21", PLOS Pathogens, Jul. 2013, vol. 9, Issue 7, e1003471, doi:10.1371/journal.ppat.1003471, pp. 1-15, 16 pages total.

Recombinant human IL21

(15 kDa)

Fc-IL21 dimer

Human IL21-Fc WT (IgG4)
homodimer
(86 kDa)

Fc-IL21 monomer

Human IL21-Fc (EW/RVT IgG4)
heterodimer
(71 kDa)

IL-21 (HETERODIMERIC FC-FUSED IL-21) FUSED TO IMMUNOGLOBULIN HEAVY CHAIN CONSTANT REGION HETERODIMER (HETERODIMERIC FC), AND PHARMACEUTICAL COMPOSITION COMPRISING SAME

CROSS REFERENCE TO RELATED APPLICATIONS

This Application is a National Stage of International Application No. PCT/KR2017/009570 filed Aug. 31, 2017, claiming priority based on Korean Patent Application No. 10-2016-0113452 filed Sep. 2, 2016.

TECHNICAL FIELD

The present invention relates to a heterodimeric Fc-fused protein comprising first and second Fc regions of an immunoglobulin heavy chain constant region (Fc) pair and in which IL-21 is bound to at least one of the N-terminus or the C-terminus of the first Fc region and/or the second Fc region, wherein CH3 domains of the first Fc region and the second Fc region are mutated such that the formation of a heterodimer is promoted, and a pharmaceutical composition comprising the heterodimeric Fc-fused protein.

When the heterodimeric Fc-fused protein according to the present invention is used, an in vivo half-life of IL-21 included in the heterodimeric Fc-fused protein may be significantly increased.

BACKGROUND ART

Human antibodies (Immunoglobulin G (IgG), IgM, IgD, IgE, and IgA) present in nature are present in the form of an assembly of two heavy chains having the same amino acid sequence and two light chains having the same amino acid sequence. In this regard, homodimerization between the same two heavy chains is induced by non-covalent interaction between the last domains (CH3 domain for IgG, IgD, and IgA, CH4 domain for IgM, and CH2 and CH4 domains for IgE) of a constant region of an antibody, and a disulfide bond between hinge regions.

The antibody-derived heterodimeric heavy chain constant region (heterodimeric Fc) technology is a technology for generating a heterodimeric Fc through engineering so as to have a bond where heterodimerization is preferred and homodimerization is not preferred or inhibited, via a specific non-covalent bond between the last domains of a constant region that greatly contribute to homodimerization of the aforementioned naturally occurring antibodies (IgG, IgM, IgA, IgD, and IgE). More specifically, through gene manipulation, mutations are induced in CH3 domains of two different antibody heavy chains so that the two heavy chains are very similar in structure to naturally occurring antibodies, have a minimal deviation in sequence, and form a heterodimer (U.S. Pat. No. 7,695,936; Korean Patent Registration No. 1,522,954). The heterodimeric Fc technology is a platform technique for producing a bispecific antibody, and most CH3 domain mutants known to induce heterodimer formation have been produced by introducing an asymmetric mutant pair based on structure-based rational design of an antibody into the CH3 domain interacting surface (Spreter Von Kreudenstein et al., 2014). As pioneering work, there is a knob-into-hole technology available from Genentech (Ridgway et al., 1996), and many multinational pharmaceutical firms have developed and reported the above platform technologies, such as ZW1 from Zymeworks (Von Kreudenstein et al., 2013), HA-TF available from XENECORE Co., Ltd (Moore G L et al., 2011), SEEDbody available from EMD Serono (Davis J H et al., 2010), and the like. Among them, an EW/RVT mutant used in the present invention is a mutant in which heterodimer formation is enhanced such that, by sequentially and structurally analyzing interactions of the above-described existing mutants, a selective electrostatic bond of the CH3 domain interaction surface (K360ECH3A-Q347RCH3B), which is a new mutation strategy, is formed, and a mutually complementary hydrophobic bond (K409WCH3A-D399VCH3B/F405TCH3B) is formed instead of existing electrostatic bonding (Choi et al. 2013; Korean Patent Registration No. 10-1522954).

All heterodimeric Fc variants having been reported to date, including the above EW/RVT variant are based on IgG1, which is the most abundant among human antibody isoforms, and there has been no report of variants for other isoforms except for IgG1 (IgG2, IgG3, IgG4, IgA, IgM, and IgM).

Since most of the therapeutic antibodies approved by the US Food and Drug Administration (FDA) and commercially available have adopted the isoform IgG1 (Irani et al., 2015), in the case of immune-modulating antibodies or receptor agonist fusion proteins, which do not require an antibody-specific effector function such as antibody-dependent cellular cytotoxicity (ADCC) or complement-dependent cellular cytotoxicity (CDC), there has recently been a trend to develop an IgG2- or IgG4-based therapeutic protein in which these effector functions are significantly reduced as compared to that of IgG1.

Meanwhile, most physiologically active proteins are often small in size and have a short half-life in the body. To address these drawbacks, attempts have been made to conjugate PEG or fuse an antibody-derived Fc (crystallizable fragment) region, but the development of a form in which the activity of a physiologically active protein is efficiently and sufficiently maintained for a long time has not been implemented. In particular, in the case of IL-21, which acts as a monomer in the natural world, it is difficult to maintain the monomeric form using existing antibody Fc regions that homodimerize. One IL-21 has activity by binding to one IL-21 receptor (IL21R) and one γc-chain.

Under such technical background, the inventors of the present invention constructed a heterodimer variant including an antibody-derived Fc region in order to mimic IL-21, which acts as a monomer, and used the heterodimer variant to develop a new therapeutic fusion protein in the form of a heterodimeric Fc-fused protein in which IL-21 was bound to the terminus of the Fc region.

Among cells used as immunotherapeutic agents, NK cells, which are innate immune cells, can kill various kinds of cancer cells and recognizes cancer cells regardless of the presence or absence of antigens, and thus have recently drawn attention as an anticancer immunotherapeutic agent. To use NK cells as an anticancer immunotherapeutic agent, it is necessary to produce a great number of natural killer cells with increased anticancer activity and to form an environment in which natural killer cells survive for a long period of time in vivo to exhibit anticancer efficacy. For this reason, attempts are being made globally to increase the viability of and induce anticancer activity in NK cells by administering cytokines (IL-2, IL-12, IL-15, IL-18, IL-21, and IFNs), which affect the activation regulation of NK cells, along with natural killer cells in vivo. However, IL-2 is the only cytokine commercially available and approved in clinical trials to be administered directly to patients to date. IL-2 increases the viability and activity of NK cells and is relatively inexpensive, while activating regulatory T cells, which are immunosuppressive cells, to inhibit anticancer immunity (Cesana et al., J Clin Oncol. 2006, Wei et al., Cancer Res. 2007). Therefore, there is an urgent need for commercialization of cytokines that activate NK cells without activating regulatory T cells.

In this regard, IL-21 has recently drawn attention in anticancer immunotherapy. It is reported that, similar to IL-2, although IL-21 promotes the proliferation and differentiation of CD4+ T cells and CD8+ T cells, it does not affect the proliferation of regulatory T cells, and thus co-administration of IL-21 with an anticancer immunotherapeutic agent is anticipated (Al-Chami et al., Cytokine, 2016). It has been reported that, with regards to NK cells, IL-21 shows the following results: 1) promotion of the proliferation of NK cells derived from human-derived CD34+ hematopoietic progenitor cells in the presence of Fms-like tyrosine kinase-3 (FLT3-L) together with IL-15 (Parrish-Novak et al., Nature, 2000); 2) promotion of extracellular expansion of NK cells and aging inhibition when the membrane bound form IL-21 is expressed in K562 cells, which are used as a trophoblast cell line (Lee D A et al., PlosOne, 2012); 3) promotion of proliferation due to IL-2 plus IL-15 during culturing of canine NK cells (Shin et al., Vet Immunol Immunopathol. 2015); 4) promotion of the expression of NKG2D receptors by activation of STAT3 in human NK cells (Zhu et al., Blood, 2014); and the like.

Accordingly, in the present invention, Fc-binding recombinant IL-21 capable of maintaining activity in vivo for a long period of time was prepared using a heterodimer method, and it was found that the prepared Fc-IL21 monomer exhibited excellent NK cell proliferation promotion as compared to water-soluble IL-21 or dimer IL-21, and could induce a superior antitumor effect to water-soluble IL-2 or dimer IL-21 in vivo via less frequent administration. A heterodimeric Fc-fused protein including the Fc-IL21 monomer of the present invention complements the disadvantage, i.e., frequent administration required when water-soluble IL-21 or IL-2 is used, and exhibits high biological anticancer activity as compared to dimer IL-21 prepared using an existing method.

SUMMARY

Therefore, the present invention has been made in view of the above problems, and it is an object of the present invention to provide a novel heterodimeric Fc-fused protein in which the activity of cytokines as monomers exhibiting physiological activity is able to be sufficiently maintained for a long period of time.

In particular, the heterodimeric Fc-fused protein according to the present invention is in a form that mimics a naturally present form of IL-21, which exhibits physiological activity as a monomer, thereby maintaining the activity of IL-21 present in nature. An Fc-IL21 monomer of the present invention exhibits excellent activity as compared to water-soluble IL-21 or dimer IL-21.

In addition, it is another object of the present invention to provide a pharmaceutical composition comprising the heterodimeric Fc-fused protein, a composition and method for treating a disease, particularly cancer by using the same, and a use of the composition therefor.

To address the above-described problems, the present invention provides a heterodimeric Fc-fused protein comprising first and second Fc regions of an immunoglobulin heavy chain constant region (Fc) pair and in which IL-21 is bound to at least one of the N-terminus or the C-terminus of the first Fc region and/or the second Fc region, wherein CH3 domains of the first Fc region and the second Fc region are mutated such that the formation of heterodimeric Fc is promoted.

The present invention also provides a pharmaceutical composition comprising the heterodimeric Fc-fused protein.

The present invention also provides a method of treating a disease, particularly cancer, which comprises administering a pharmaceutical composition comprising the heterodimeric Fc-fused protein.

The present invention also provides a use of a pharmaceutical composition comprising the heterodimeric Fc-fused protein for treating a disease, particularly cancer.

DETAILED DESCRIPTION AND EXEMPLARY EMBODIMENTS

Figure 1:
FIG. 1 is a view illustrating the form of recombinant human IL-21 to be fused to a heavy chain constant region.

Unless otherwise defined, all technical and scientific terms used in the present specification have the same meaning as commonly understood by one of ordinary skill in the art to which the present invention pertains. In general, the nomenclature used herein is well known and commonly used in the art.

According to an embodiment of the present invention, there is provided a heterodimeric Fc-fused protein comprising first and second Fc regions of an immunoglobulin heavy chain constant region (Fc) pair and in which IL-21 is bound to one of the N-terminus and the C-terminus of the first Fc region or the second Fc region, wherein CH3 domains of the first Fc region and the second Fc region are mutated such that the formation of heterodimeric Fc is promoted.

Preferably, the heterodimeric Fc-fused protein is a heterodimeric Fc-fused protein in which IL-21 is bound to only any one of the N-terminus and the C-terminus of the first Fc region or the second Fc region.

The term "Fc region" or "heavy chain constant region" as used herein refers to a region including a CH2 domain, a CH3 domain, and a hinge domain, which are derived from an antibody.

The expression "CH3 domains of the first Fc region and the second Fc region are mutated such that the formation of a heterodimer is promoted" as used herein means that a mutation is induced in some of the sequence of two Fc regions of antibodies present in nature in the form of a homodimer having the same sequence to be mutated such that the formation of a heterodimer is promoted via a non-covalent bond between the first Fc region and the second Fc region, and the formation of a homodimer is reduced or preferably barely occurs.

Preferably, the mutation of the first Fc region and the second Fc region according to the present invention such that the formation of heterodimeric Fc is promoted may include mutation of respective CH3 domains included in the antibody-derived first and second Fc regions such that the formation of a heterodimer is promoted.

The term "heterodimeric Fc" or "Fc heterodimer" as used herein refers to a heterodimer comprising a first Fc region and a second Fc region, wherein CH3 domains of the first Fc region and the second Fc region are mutated such that the formation of heterodimeric Fc is promoted.

Each of the first Fc region and the second Fc region of the present invention may be derived from an Fc region selected from the group consisting of human IgG1, IgG2, IgG3, IgG4, IgM, IgA, IgD, and IgE, and preferably, each of the first Fc region and the second Fc region is derived from IgG1, IgG2, IgG3, or IgG4.

In addition, the first Fc region and the second Fc region are derived from an isotype antibody.

In another embodiment, the mutation of the CH3 domains may include one or more mutations selected from the following group. All mutation sites of the present invention are in accordance with the EU index.

(1) amino acid residue substitution at position K360 of the CH3 domain of the first Fc region; and amino acid residue substitution at position Q347 of the CH3 domain of the second Fc region; and/or (2) amino acid residue substitution at position K409 of the CH3 domain of the first Fc region; and amino acid residue substitution at position F405 and/or D399 of the CH3 domain of the second Fc region.

Preferably, the amino acid residue substitution at position K360 of the CH3 domain of the first Fc region may be K360E, and the amino acid residue substitution at position Q347 of the CH3 domain of the second Fc region may be Q347R, and the amino acid residue substitution at position K409 of the CH3 domain of the first Fc region may be K409W, the amino acid residue substitution at position F405 of the CH3 domain of the second Fc region may be F405T, and the amino acid residue substitution at position D399 of the CH3 domain of the second Fc region may be D399V.

Most preferably, the mutation of the CH3 domain of the first Fc region or the second Fc region may include one or more mutations selected from the following groups (mutation sites are in accordance with the EU index):

(1) K360E amino acid residue substitution at position K360 of the CH3 domain of the first Fc region;

(2) Q347R amino acid residue substitution at position Q347 of the CH3 domain of the second Fc region;

(3) K409W amino acid residue substitution at position K409 of the CH3 domain of the first Fc region; and (4) F405T amino acid residue substitution at position F405 of the CH3 domain of the second Fc region and D399V amino acid residue substitution at position D399 of the CH3 domain of the second Fc region.

Preferably, the CH3 domain included in each of the antibody-derived first and second Fc regions according to the present invention may have a sequence selected from amino acid sequences represented by SEQ ID NOS: 1 and 2.

In particular, the antibody-derived first and second Fc regions according to the present invention may have IgG4-derived CH3 domain sequences shown in Table 1 below.

TABLE 1

| Configuration | CH3 sequence of first Fc region (EU number 341-447) | CH3 sequence of second Fc region (EU number 341-447) |
|---|---|---|
| IgG4-EW/RVT | GQPREPQVYTLPPSQEEMTENQVSLTC LVKGFYPSDIAVEWESNGQPENNYKTT PPVLDSDGSFFLYSWLTVDKSRWQEGN VFSCSVMHEALHNHYTQKSLSLSLGK (SEQ ID NO: 1) | GQPREPRVYTLPPSQEEMTKNQVSLTC LVKGFYPSDIAVEWESNGQPENNYKTT PPVLVSDGSFTLYSRLTVDKSRWQEGN VFSCSVMHEALHNHYTQKSLSLSLGK (SEQ ID NO: 2) |

According to another embodiment, the present invention provides a pharmaceutical composition comprising the heterodimeric Fc-fused protein according to the present invention. The pharmaceutical composition according to the present invention is a pharmaceutical composition for treating cancer, which comprises a heterodimeric Fc-fused protein containing IL-21 as a physiologically active protein.

Cancer treatable using the pharmaceutical composition for treating cancer, which comprises a heterodimeric Fc-fused protein containing IL-21 may be selected from the group consisting of colon cancer, melanoma, breast cancer, pancreatic cancer, kidney cancer, prostate cancer, ovarian cancer, small intestine cancer, esophageal cancer, cervical cancer, lung cancer, lymphoma, and blood cancer, but the present invention is not limited thereto.

The pharmaceutical composition according to the present invention may further include a pharmaceutically acceptable carrier. The term "pharmaceutically acceptable carrier" refers to a substance that may be added to the active ingredient to aid in formulating or stabilizing a preparation, and the carrier does not cause a toxic effect that is significantly harmful to patients.

The carrier refers to a carrier or diluent that does not irritate patients and does not hinder the biological activity and characteristics of the heterodimeric Fc-fused protein according to the present invention. As a pharmaceutically acceptable carrier in a composition formulated into a liquid solution, which is suitable for sterilization and a living body, one selected from saline, sterilized water, Ringer's solution, buffered saline, an albumin injection solution, a dextrose solution, a maltodextrin solution, glycerol, and ethanol, or a mixture of two or more of these ingredients may be used. If necessary, other general additives such as an antioxidant, a buffer, a bacteriostatic agent, and the like may be added. In addition, a diluent, a dispersant, a surfactant, a binder, and a lubricant may be further added to the composition to be formulated into an injectable preparation such as an aqueous solution, a suspension, an emulsion, or the like, pills, capsules, granules, or tablets. Other carriers may be described in, for example, Remington's Pharmaceutical Sciences (E. W. Martin).

The pharmaceutically acceptable carrier includes a sterile aqueous solution or dispersion and sterile powder for extemporaneous administration of a sterile injectable solution or dispersion. The use of these media and agents for pharmaceutically active materials is known in the art. The composition is preferably formulated for non-oral injection. The composition may be formulated as a solution, a microemulsion, a liposome, or other customized structures suitable for high drug concentrations. Examples of the pharmaceutically acceptable carrier include solvents or dispersion media including water, ethanol, polyols (e.g., glycerol, propylene glycol, liquid polyethylene glycol, and the like), and suitable mixtures thereof. In some cases, the composition may include an isotonic agent such as sugars, or polyalcohols such as mannitol, sorbitol, or sodium chloride. The sterile injectable solution may be prepared by incorporating a required amount of the heterodimeric Fc-fused protein in an appropriate solvent, if needed, along with one of the above-listed ingredients or a combination thereof, and then performing sterile microfiltration thereon. Generally, the dispersion is prepared by incorporating the active compound into a sterile vehicle including a basic dispersion medium and other needed ingredients from those described above. In the case of sterile powder for the preparation of a sterile injectable solution, some preparation processes involve vacuum drying and freeze-drying (lyophilization), in which the active ingredient and any additional desired ingredient powder are produced from a pre-sterilized and pre-filtered solution.

In addition, the pharmaceutical composition according to the present invention may be orally or parenterally administered at a dose and frequency that may vary depending on the severity of a suffering patient. The composition may be administered to a patient as a bolus or via continuous injection, if needed. In another embodiment, the pharmaceutical composition according to the present invention may be administered intrarectally, intravenously, subcutaneously, intrauterinely, or intracerebrovascularly.

In addition, the pharmaceutical composition for treating cancer, which comprises the heterodimeric Fc-fused protein containing IL-21 may be used for co-treatment together with other anticancer agents, and the other anticancer agents may be cytotoxic T cells and/or natural killer (NK) cells, but the present invention is not limited thereto. That is, all anticancer agents that may be used in other technical fields may be used for co-treatment.

In particular, in a case in which the pharmaceutical composition for treating cancer which comprises the heterodimeric Fc-fused protein containing IL-21 is used for co-treatment with cytotoxic T cells and/or natural killer (NK) cells, this case may enable 1) preservation of the proliferative ability of NK cells induced by IL-21 in vitro;

2) induction of a significant increase in anticancer activity upon co-administration with NK cells in vivo, as compared to a group treated only with IL-21; or 3) replacement of frequent in vivo administration required due to a short half-life of IL-21 and other gamma-chain cytokines (e.g., IL-2, IL-7, IL-15, and the like).

In a case in which the above-described pharmaceutical composition for treating cancer is co-administered with natural killer (NK) cells, the heterodimeric Fc-fused protein containing IL-21 as a monomer exhibits significantly high activity as compared to water-soluble IL-21 or dimer IL-21.

According to another embodiment, the present invention provides a method of treating a disease which comprises administering the pharmaceutical composition comprising the heterodimeric Fc-fused protein according to the present invention to a patient in need of treatment.

Preferably, in a case in which a physiologically active protein included in the heterodimeric Fc-fused protein according to the present invention is IL-21, more preferably monomer IL-21, the present invention provides a method of treating a patient with cancer, particularly cancer selected from the group consisting of colon cancer, melanoma, breast cancer, pancreatic cancer, kidney cancer, prostate cancer, ovarian cancer, small intestine cancer, esophageal cancer, cervical cancer, lung cancer, lymphoma, and blood cancer.

EXAMPLES

Hereinafter, the present invention will be described in further detail with reference to the following examples. It will be obvious to those of ordinary skill in the art that these examples are provided for illustrative purposes only and are not intended to limit the scope of the present invention in accordance with the essence of the present invention.

Example 1: Design of CH3 Domain Variant for Formation of Heterodimer for Each Human Antibody Isoform (Sequencing)

Figure 4:
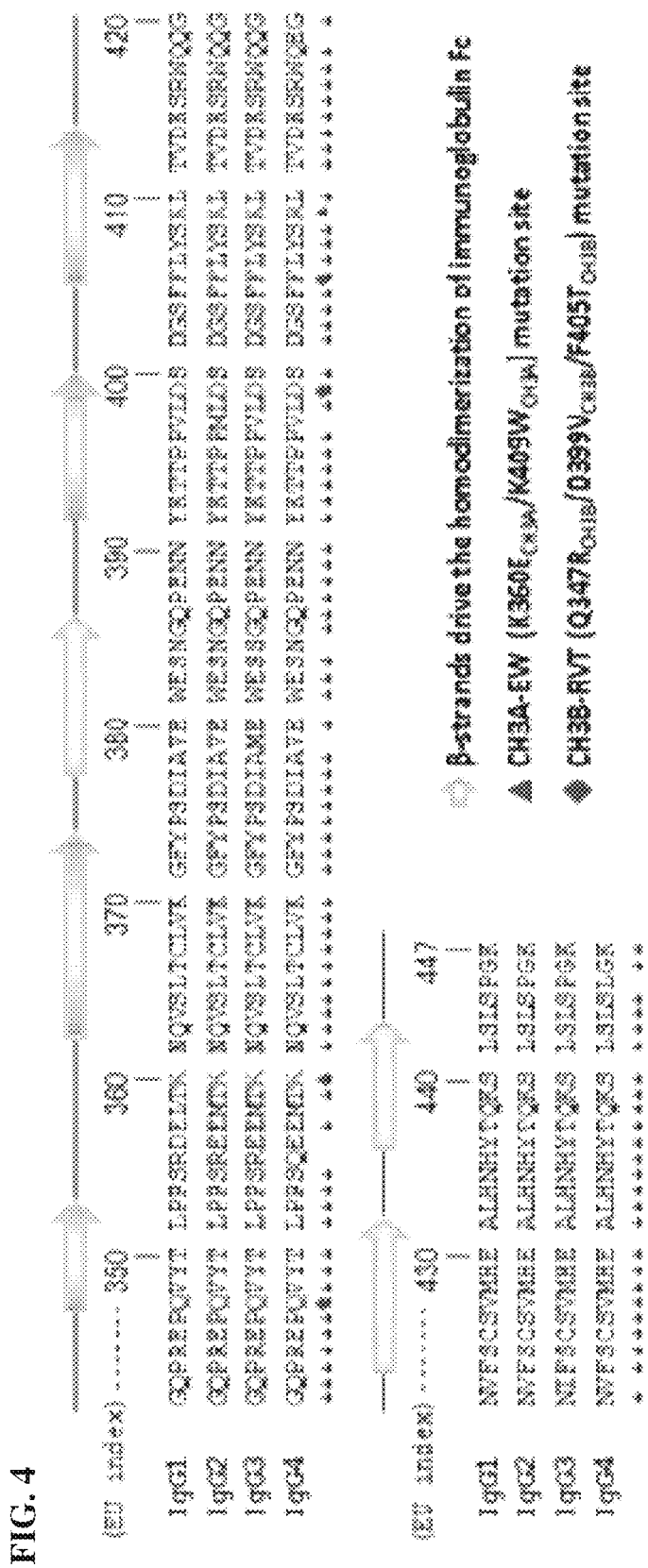
FIG. 4 illustrates results of listing and comparing the sequence (IgG1: SEQ ID NO: 4; IgG2: SEQ ID NO: 5; IgG3: SEQ ID NO: 6; IgG4: SEQ ID NO: 7) of a CH3 domain for each of human antibody immunoglobulin G isoforms and selecting potential mutation sites, in order to construct a CH3 domain variant for the formation of a heterodimer for each human antibody isoform.

To prepare a fragment of a human antibody heavy chain constant region (Fc) heterodimer into which CH3 domain mutation, in which heterodimer formation is preferred, is introduced, first, the similarity of amino acid sequences between human antibody isoforms of the CH3 domain, which plays a major role in interactions for heterodimer formation, was analyzed. At this time, a variant pair (EW/RVT) induced in heterologous CH3A:CH3B (in the present invention, CH3A and CH3B respectively mean the CH3 region of the first Fc region and the CH3 region of the second Fc region) enables the formation of CH3A:CH3B with a high yield, as a strategy for promoting the formation of an Fc heterodimer, which is disclosed in existing documents or patents (Choi et al., 2013; KR 10-1522954). FIG. 4 illustrates results of listing and comparing the sequence of the CH3 domain of each human antibody immunoglobulin G (IgG) isoform (IgG1: SEQ ID NO: 4; IgG2: SEQ ID NO: 5; IgG3: SEQ ID NO: 6; and IgG4: SEQ ID NO: 7).

heterodimer based on IgG4 and into which the EW/RVT mutation was introduced thereinto, was used. Previous reports have shown that in the construction of immunocytokines, which are fused forms of antibodies and cytokines, the intrinsic function of IgG1, such as ADCC/CDC, rather promotes clearance in vivo. Thus, a fusion protein was constructed using the isoform IgG4 in which the function of ADCC/CDC was barely exhibited as compared to IgG1 (Gillies S D et al., 1999).

TABLE 2

| Configuration | CH3A chain<br>CH3 sequence of first Fc region (EU number 341-447) | CH3B chain<br>CH3 sequence of second Fc region (EU number 341-447) |
|---|---|---|
| IgG1 Wild type | GQPREPQVYTLPPSRDELTKNQVSLTCLVKG<br>FYPSDIAVEWESNGQPENNYKTTPPVLDSDG<br>SFFLYSKLTVDKSRWQQGNVFSCSVMHEALH<br>NHYTQKSLSLSPGK<br>(SEQ ID NO: 4) | Same as SEQ ID NO: 7 |
| IgG2 Wild type | GQPREPQVYTLPPSREEMTKNQVSLTCLVKG<br>FYPSDIAVEWESNGQPENNYKTTPPMLDSDG<br>SFFLYSKLTVDKSRWQQGNVFSCSVMHEALH<br>NHYTQKSLSLSPGK<br>(SEQ ID NO: 5) | Same as SEQ ID NO: 10 |
| IgG3 Wild type | GQPREPQVYTLPPSREEMTKNQVSLTCLVKG<br>FYPSDIAMEWESSGQPENNYKTTPPVLDSDG<br>SFFLYSKLTVDKSRWQQGNIFSCSVMHEALH<br>NHYTQKSLSLSPGK<br>(SEQ ID NO: 6) | Same as SEQ ID NO: 13 |
| IgG4 Wild type | GQPREPQVYTLPPSQEEMTKNQVSLTCLVKG<br>FYPSDIAVEWESNGQPENNYKTTPPVLDSDG<br>SFFLYSRLTVDKSRWQEGNVFSCSVMHEALH<br>NHYTQKSLSLSLGK<br>(SEQ ID NO: 7) | Same as SEQ ID NO: 16 |

As a result of sequence comparison, it can be confirmed that Q347, K360, D399, F405, and K409 residues, which are in bold, are mutation-introduced residues, and almost similar residues are conserved regardless of the subtypes of human antibody IgG. Thus, it was found that mutations induced for the formation of a heterodimeric CH3 variant pair are not limited to human antibody IgG1. Each amino acid sequence was confirmed in the International ImMunoGeneTics information system (IMGT; URL: http://www.imgt.org/), and numbering of all amino acid sites in the present invention is in accordance with the EU index (numbering).

Example 2: Construct of Human Fc-IL21 Fusion Protein

Figure 5:
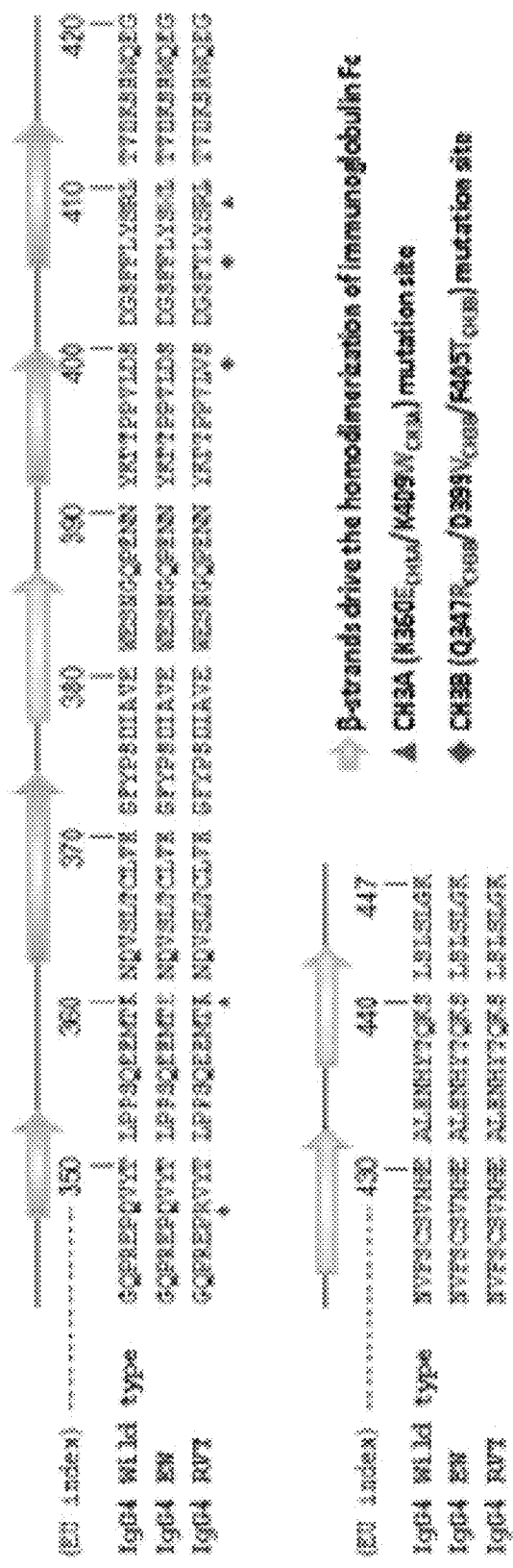
FIG. 5 illustrates sequence information (IgG4 wild type: SEQ ID NO: 7; IgG4 EW: SEQ ID NO: 1; and IgG4 RVT: SEQ ID NO: 2) of a wild type- and variant-introduced heterodimeric Fc pair of an IgG4 CH3 domain.

Among the isoform variants of FIG. 5, which were expected that heterodimer formability would be maintained at a level similar to that of previously reported IgG1-based EW/RVT Fc heterodimeric variants, a human interleukin 21 (IL-21, SEQ ID NO: 3)-fusion protein was constructed using an IgG4-based variant (IgG4-EW/RVT, SEQ ID NOS: 1 and 2). IL-21, which is present in nature, is a cytokine acting as a monomer, and one IL-21 has activity by binding to one IL-21 receptor (IL21R) and one γc-chain. Therefore, by using the IgG4-EW/RVT heterodimeric variant, one IL-21 was linked to only one of different heterodimeric Fc variants (CH3A or CH3B) to maintain the monomeric form of IL-21 present in nature.

Figure 2:
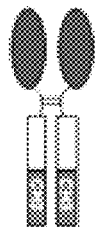
FIG. 2 is a view illustrating an Fc-IL21 dimer form in which human IL-21 is fused to wild-type IgG4 Fc.
Figure 3:
FIG. 3 is a view illustrating an Fc-IL21 monomer form in which human IL-21 is fused to an EW/RVT variant produced based on IgG4.

As the Fc heterodimeric variant for the construction of a fusion protein, IgG4-EW/RVT, which was formed as a FIGS. 1 to 3 illustrate a recombinant protein of IL-21, an IL-21 dimer fusion protein using wild-type Fc, and an IL-21 monomer fusion protein using EW/RVT. Thereamong, a fusion protein into which a CH3 variant pair was introduced, which was constructed in the present invention, is illustrated in FIG. 3.

IL21-Fc (IgG4 EW) and Fc (IgG4 RVT), into which the CH3 variant pair was introduced, was in-frame cloned into pcDNA3.1(+) (Invitrogen, USA), which is an animal cell expression vector having a CMV promotor, using NotI/HindIII so as to have signal sequence-IL21 mature form-Hinge-CH2-CH3 or signal sequence-Hinge-CH2-CH3. IL-21 used herein was human IL-21 (Uniprot entry name, Q9HBE4; SEQ ID NO: 3), and only a DNA sequence encoding a mature form except for the signal sequence was used. In particular, human IL-21 was linked to Fc using a hinge region without an additional peptide linker to facilitate interaction with the IL-21 receptor. The hinge region used herein was a commonly used IgG1-derived hinge, and cysteine residues in the upper hinge region except for cysteine residues in the core hinge region for dimer formation were substituted with serine residues to prevent unwanted disulfide bonds from being formed during protein fusion.

In particular, a CH2 domain of the Fc used in the present invention is an IgG2/4 hybrid. The IgG2/4 hybrid is in a fused form of the lower hinge portion of IgG2 and the CH2 portion of IgG4. This is a domain derived from eculizumab antibody (Product Name: Soliris) which targets complement C5 and is a domain designed to inhibit the ability of binding to an Fc receptor according to the purpose of use of the antibody (to completely eliminate a CDC function) (Robert A et al., 2009).

Figure 6:
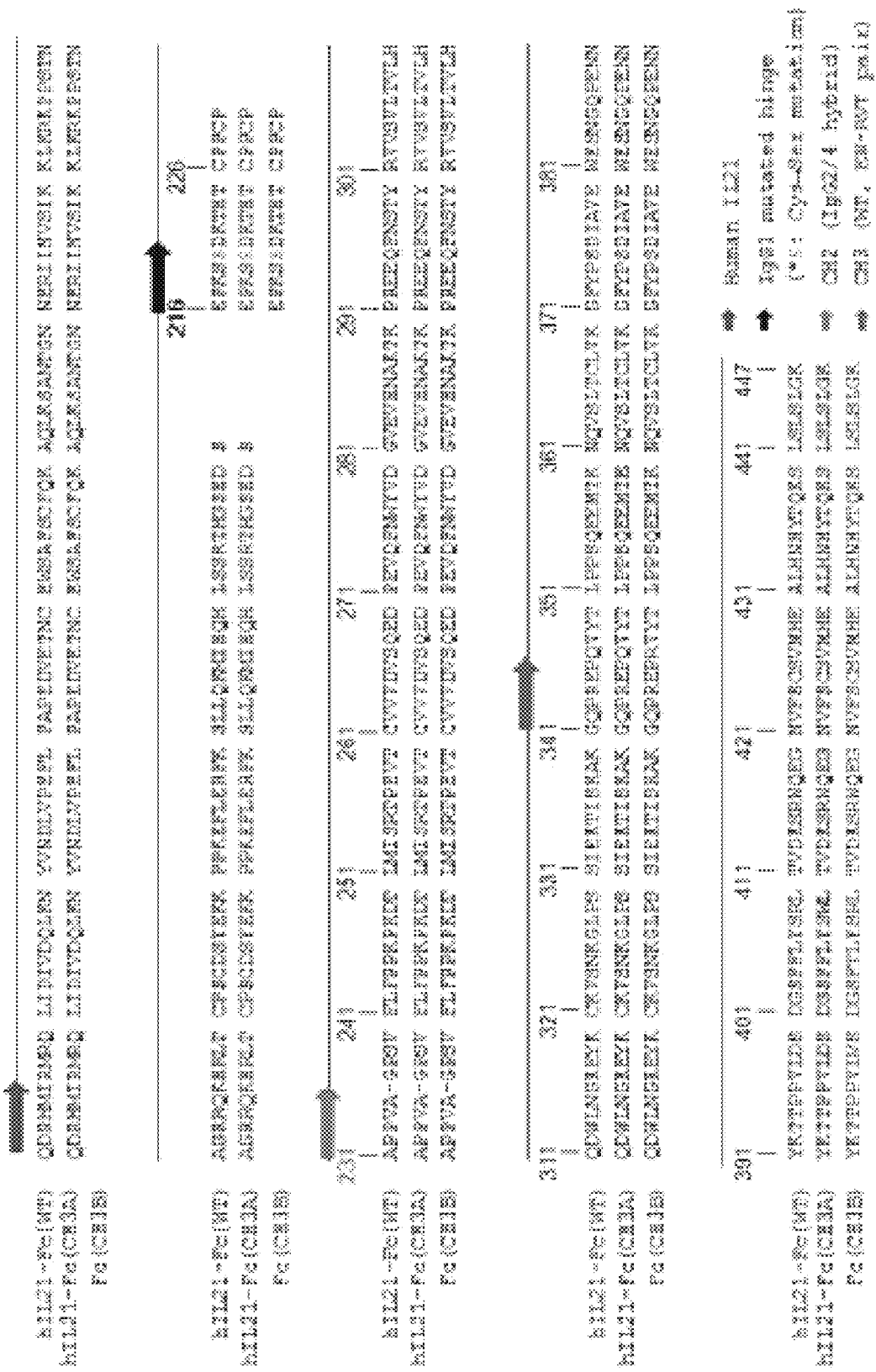
FIG. 6 illustrates sequence information of wild-type Fc and a heterodimeric Fc pair that were fused with IL-21 used to construct an Fc-IL21 dimer and an Fc-IL21 monomer.
Figure 7:
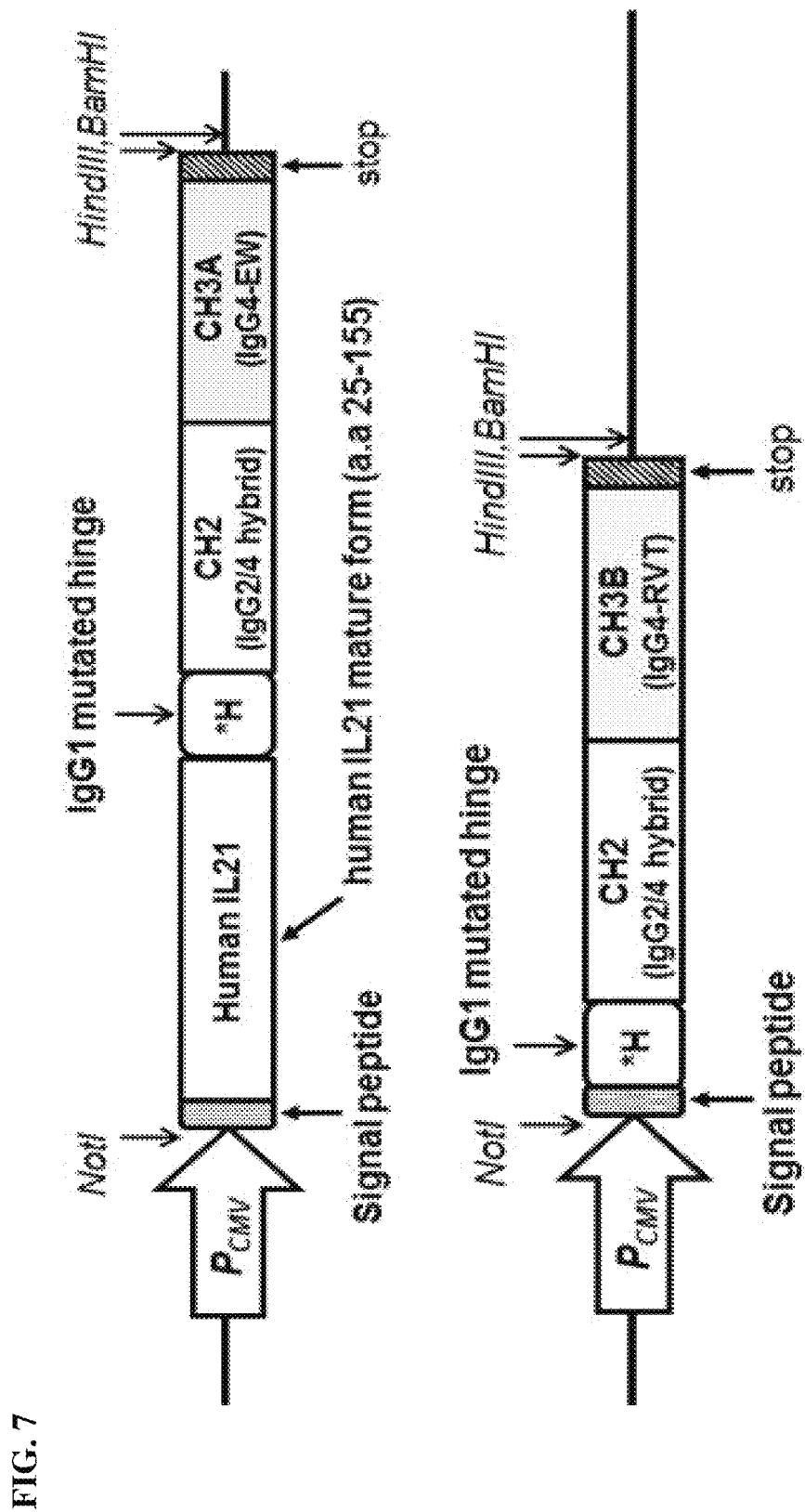
FIG. 7 is a view illustrating a vector for expressing and purifying the fusion protein of FIG. 3 in animal cells.
Figure 8:
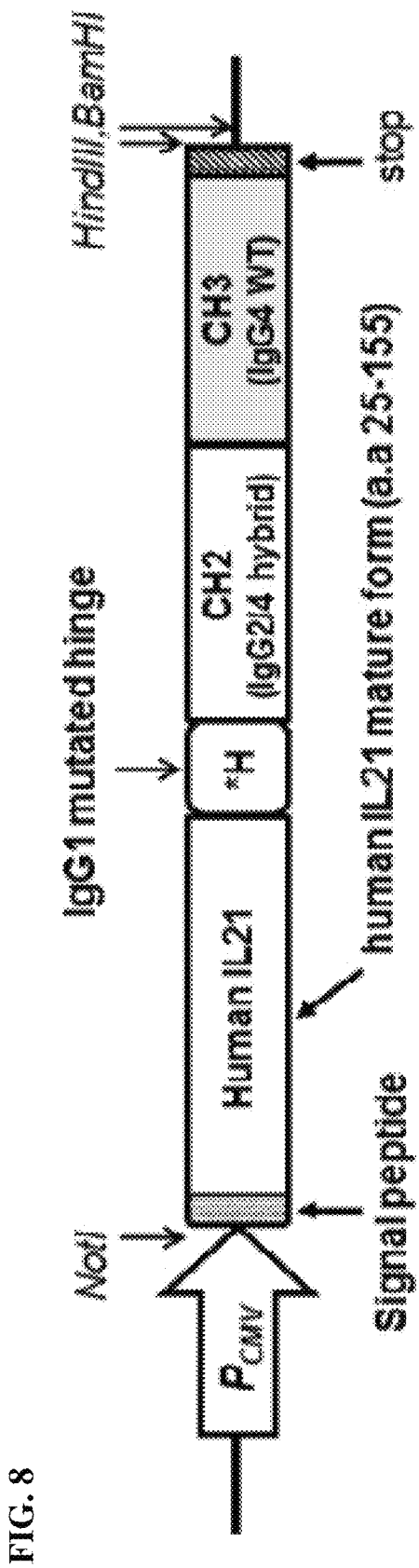
FIG. 8 is a view illustrating a vector for expressing and purifying the fusion protein of FIG. 2 in animal cells.

As a comparative example for FIG. 3, Fc-IL21 dimer (FIG. 2), in which wild-type Fc was fused, was constructed. As illustrated in FIG. 8, a DNA sequence encoding the human IL-21 mature form was in-frame cloned into an animal cell expression vector containing wild-type IgG4 CH3, with restriction enzymes NotI/HindIII by using a method similar to that described above. At this time, the used hinge region and CH2 domain also have the same sequence as that used in constructing the Fc-IL21 monomer (see FIG. 6).

Table 3 shows an amino acid sequence for the human IL-21 mature form used in construction of the fusion protein.

TABLE 3

| Config-uration | Amino acid sequence (a.a. 25-155) |
|---|---|
| Mature human IL-21 | QDRHMIRMRQLIDIVDQLKNYVNDLVPEFLPAPEDVEINCEWSAFSCFQKAQLKSA NTGNNERIINVSIKKLKRKPPSTNAGRRQKHRLTCPSCDSYEKKPPKEFLERFKSL LQKMIHQH LSSRTHGSEDS (SEQ ID NO: 3) |

Example 3: Expression/Purification of Fc-IL21 Fusion Protein

The Fc-IL21 monomer fusion protein of FIG. 3 was prepared by transiently transfecting HEK293-F (Invitrogen) cells with a mixture of IgG4 CH3A (EW) and IgG4 CH3B (RVT) expression vectors fused with human IL-21 and polyethylenimine (PEI) (Polyscience) in a ratio of 1:1 and culturing the cells in a shake flask containing a serum-free FreeStyle 293 expression medium (Invitrogen). The method will be described in detail as follows.

Upon 200 mL transfection in a shake flask (Corning), HEK293-F cells were seeded in 180 ml of a medium at a density of $1.0 \times 10^6$ cells/ml and cultured at 130 rpm and 8% $CO_2$. After 24 hours, to produce a fusion protein including each Fc variant, the corresponding CH3A and CH3B plasmids were diluted in 10 ml of a FreeStyle 293 expression medium (Invitrogen) with a total of 250 μg (2.5 μg/ml) of 125 μg of CH3A and 125 μg of CH3B, mixed with 10 ml of a medium diluted with 750 μg of PEI (7.5 μg/ml), and allowed to react at room temperature for 10 minutes. Subsequently, when the resulting mixed medium was added to the above-described cells seeded in 180 ml of the medium and the cells were cultured for a minimum of 5 days to a maximum of 7 days, proteins produced by the cells, i.e., fusion proteins including Fc variants were secreted outside of the cells and accumulated in the medium. Therefore, the proteins were purified from a cell culture supernatant collected by centrifugation at 2,500 rpm for 20 minutes after cell culture, using a protein A Sepharose column (GE healthcare). At this time, the purification method was in accordance with a standard protocol provided by the protein A column manufacturer, absorbance at 562 nm of the purified proteins was measured using a solution in a BCA protein assay kit (Thermo), and the amounts thereof were quantified according to the drawn standard curve.

Figure 9:
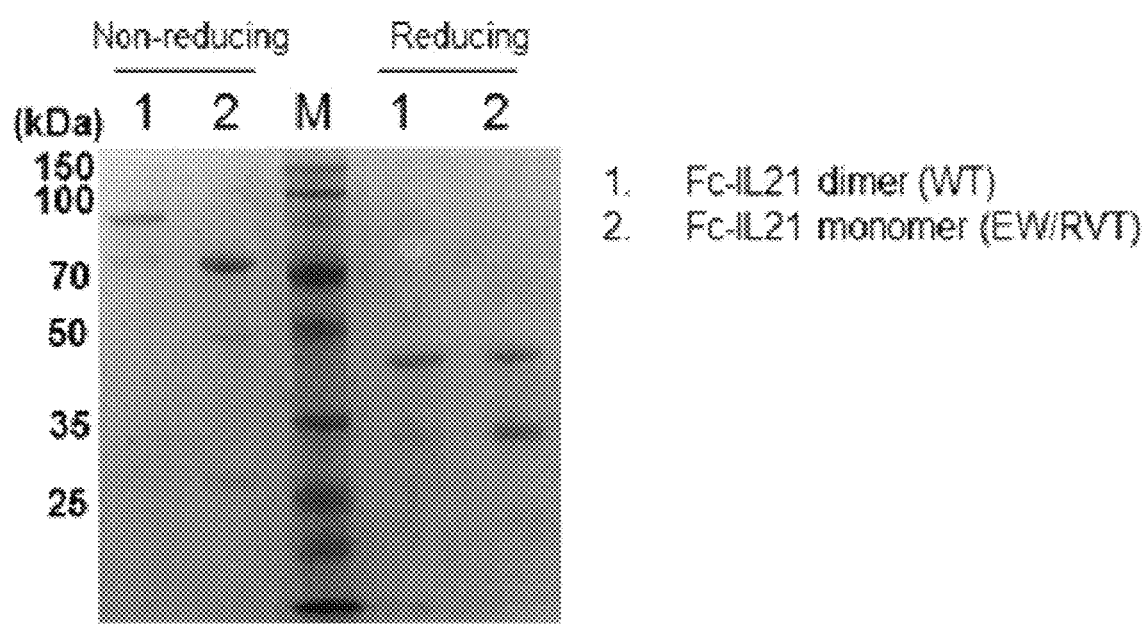
FIG. 9 illustrates results obtained by temporarily expressing and purifying the animal cell expression vectors of FIGS. 7 and 8 in HEK293F cells via co-transfection, separating 3 µg of proteins on SDS-PAGE under non-reducing and reducing conditions, and then analyzing the sizes and combination forms of the proteins through Coomassie Blue staining.

3 μg of the purified Fc-IL21 monomer and Fc-IL21 dimer fusion proteins were analyzed on SDS-PAGE under 12% non-reducing and reducing conditions (see FIG. 9). Under the non-reducing condition, the Fc-IL21 monomer was observed at 71 kDa and the Fc-IL21 dimer was observed at 86 kDa, and under the reducing condition, in the case of the Fc-IL21 dimer fused with IL-21 and consisting only of wild-type Fc, only a single band was observed at 43 kDa, while two bands were observed at 43 kDa and 28 kDa in the case of the Fc-IL21 monomer consisting of two plasmids of the IL-21-fused Fc variant CH3A (EW) and the Fc variant CH3B (RVT) not fused with IL-21.

Table 4 shows purification yields of the expressed Fc-IL21 monomer and Fc-IL21 dimer fusion proteins. The result values were expressed as the mean standard error (mean±SD) after three independent experiments. It was confirmed that the Fc-IL21 monomer form exhibited a purification yield about 17 times that of the Fc-IL21 dimer form.

TABLE 4

| Fusion protein name | Purification yield (per liter) |
|---|---|
| Fc-IL21 dimer | 3.61 ± 2.0 |
| Fc-IL21 monomer | 64.3 ± 6.6 |

Example 4: Evaluation of NK Cell Proliferative Ability of Human Fc-IL21 Fusion Protein While peripheral blood mononuclear cells, radiation-irradiated Jurkat cells, and EBV-LCL cells were cultured in the presence of the human IL-21 fusion protein of Example 3, induction of improvement in the proliferation and function of NK cells was confirmed.

In vitro expansion of natural killer cells was prepared by the following method. Human blood was collected and centrifuged at 2,500 rpm for 30 minutes using Ficoll (Ficoll-Paque™ PLUS, GE healthcare), and then peripheral blood mononuclear cells were isolated from the buffy coat. Subsequently, the Jurkat cell line and the EBV-LCL cell line, which had been irradiated with radiation at 100 Gy, were co-cultured in an hRPMI medium in which 10% FBS and 1% penicillin/streptomycin were added to an RPMI1640 medium in a ratio of 1:0.5:0.5, in the presence of 500 U/ml of IL-2. At this time, each cell line was treated with 1.25 μM of IL-21 or Fc-IL21 (monomer or dimer) and cultured. Thereafter, culturing was performed while the medium was replaced with an hRPMI medium to which 500 U/ml of IL-2 was added, once every 4 days. When the medium was replaced, the number of cells was calculated using a hematocytometer and cultured for about 3 weeks at a density of $2.5 \times 10^5$ cells/ml (Korean Patent No. 1643165).

Figure 10A:
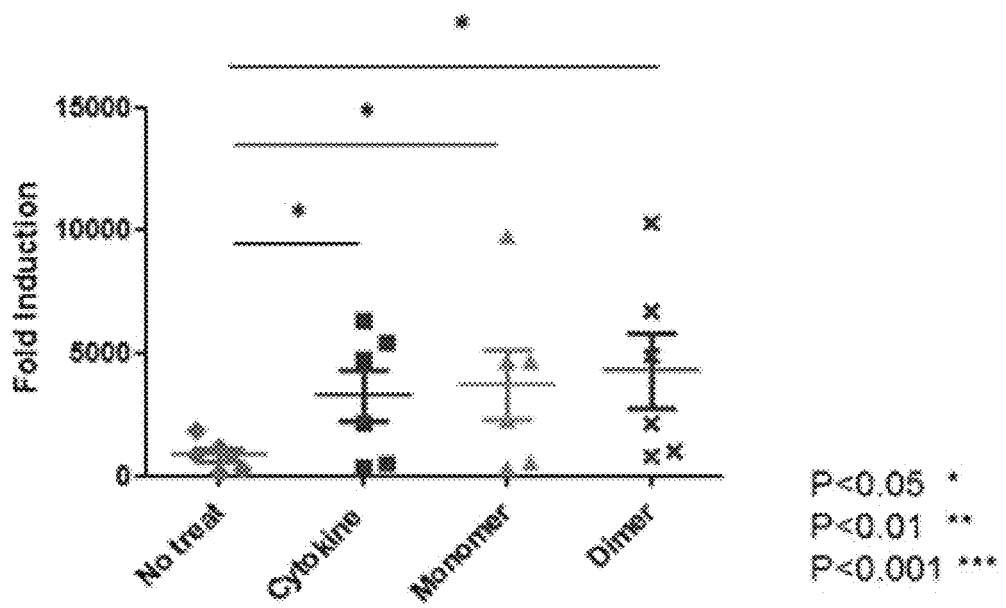
FIG. 10A illustrates growth curves and expandability of natural killer cells as a result of performing an experiment by treating the cells with an Fc-IL21 monomer or an Fc-IL21 dimer and culturing the treated cells at the time of in vitro expansion of the natural killer cells from human blood.
Figure 10B:
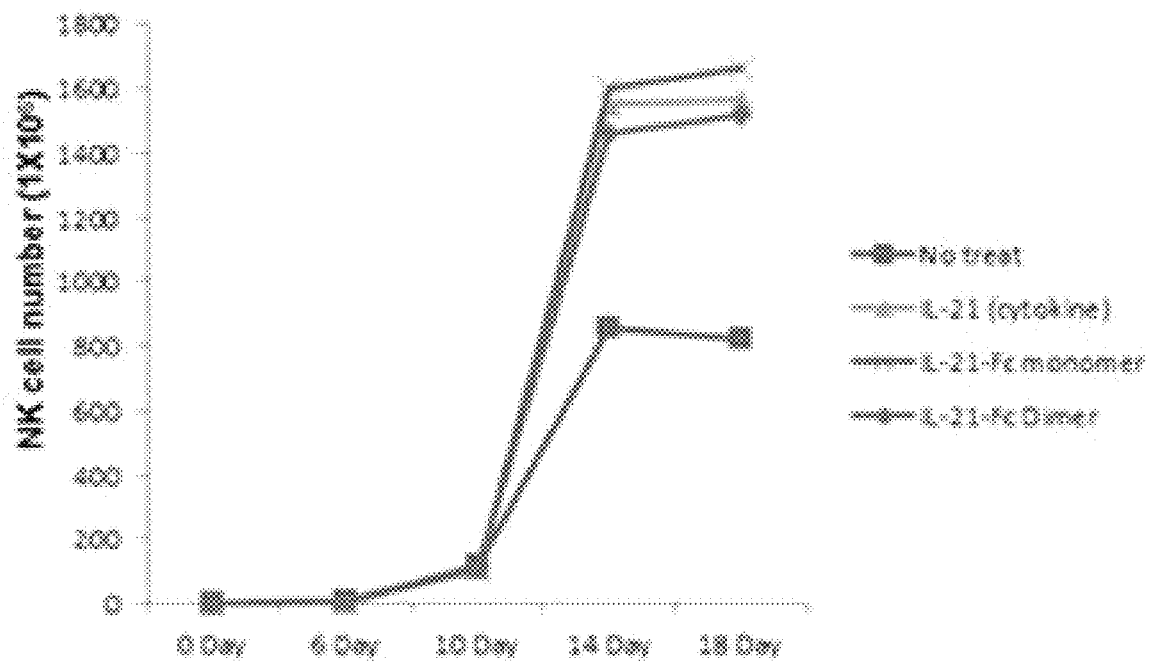
FIG. 10B illustrates results obtained by performing statistical processing on repeatedly performed experimental results from 6 donors.

As a result, it was confirmed that upon in vitro expansion of natural killer cells from human blood, when the cells were cultured after being treated with the Fc-IL21 monomer or the Fc-IL21 dimer, both the Fc-IL21 monomer and the Fc-IL21 dimer exhibited a 2-fold or more increase in expandability of natural killer cells similar to water-soluble IL-21 (see FIG. 10A and Table 5). In addition, it was confirmed that even when the process was repeatedly performed on NK killer cells from 6 donors, the cases of culturing the cells after addition of IL-21, the Fc-IL21 monomer, or the Fc-IL21 dimer exhibited significantly enhanced proliferative expansion ability (see FIG. 10B).

TABLE 5

|  | D + 18 Fold Change |
| --- | --- |
| No treatment | 1146 |
| IL-21 (cytokine) | 2186 |
| Fc-IL21 monomer | 2322 |
| Fc-IL21 dimer | 2120 |

That is, it was confirmed that, when the Fc-IL21 monomer was additionally added upon in vitro expansion and culture of a natural killer cellular therapeutic agent, a large amount of natural killer cells could be induced as compared to existing methods.

Example 5: Evaluation of Inhibitory Effect of Human Fc-IL21 Fusion Protein on In Vivo Tumor Growth It was examined whether the effect of the human IL-21 fusion protein of Example 3 on NK cell proliferation was exhibited in the same manner in vivo.

Figure 12A:
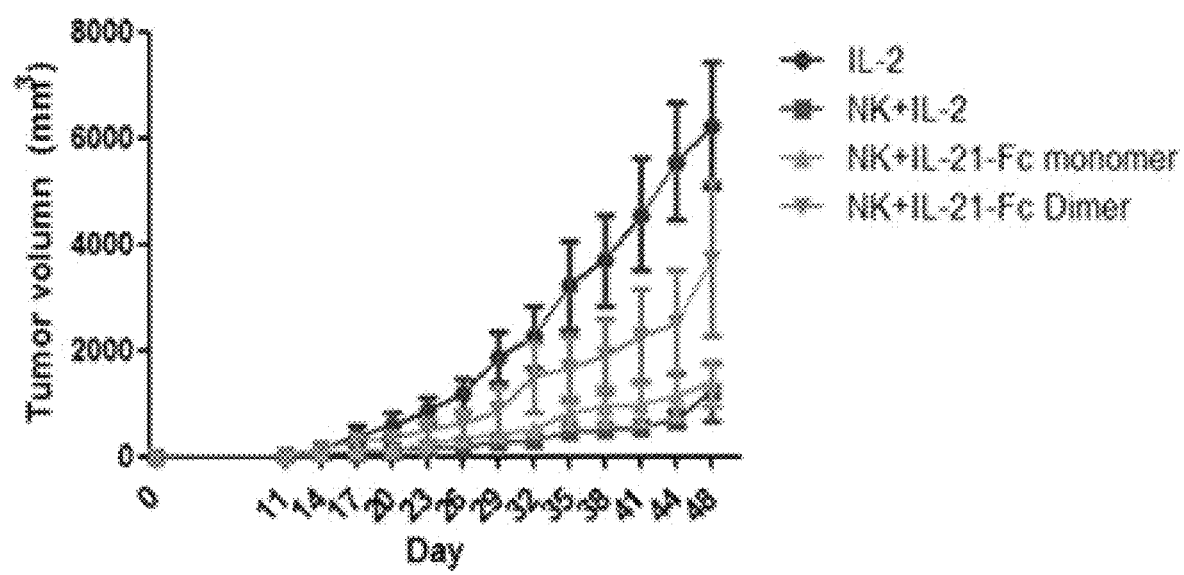
FIG. 12A illustrates results of comparing the sizes of tumors as a co-treatment effect between NK cells and IL-2, an Fc-IL21 monomer, or an Fc-IL21 dimer in a xenograft human melanoma cancer model.

FIG. 12 illustrates results of measuring tumor growth inhibitory activity in mice by using an animal cancer model.

Figure 11:
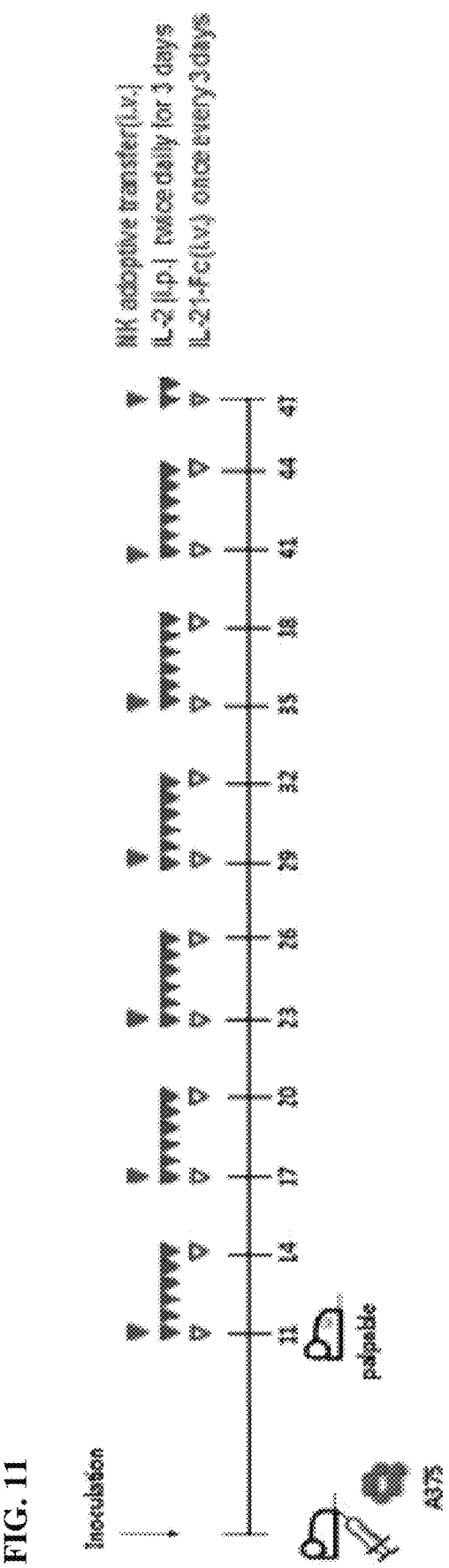
FIG. 11 is a diagram illustrating a co-treatment effect between NK cells and IL-2, an Fc-IL21 monomer, or an Fc-IL21 dimer after construction of a xenograft human melanoma cancer model, and administration methods of an NK cell therapeutic agent, IL-2, and Fc-IL21.

In particular, tumors were induced by subcutaneously injecting $2.5 \times 10^6$ cells of the melanoma cell line A375 into 6- to 7-week-old immunodeficient mice (Nude). When tumors were formed after 11 days, the Fc-IL21 monomer or the Fc-IL21 dimer was intravenously injected into the cells at the same molar concentration (~580 μM) once every three days, $1 \times 10^7$ NK cells were intravenously injected thereinto once every 6 days, and then the size of tumors was measured once every 3 days (see FIG. 11). The NK cells were intravenously administered once every 6 days, IL-2 was intraperitoneally injected twice a day, and Fc-IL21 was intravenously administered once every three days. As a control, IL-2 was administered at 5,000 IU six times for a total of three days from the administration day of NK cells. Upon administration to the animal cancer model, Fc-IL21 was diluted in phosphate buffered saline (PBS) and administered intravenously at a dose of 10 μg (~580 μM) with respect to the Fc-IL21 dimer.

A non-administered group was compared with the NK+IL-2-administered group, an NK cellular therapeutic effect of which had previously been verified, the NK+Fc-IL21 monomer-administered group, and the NK+Fc-IL21-administered group. As a result, it was confirmed that, as compared to the control, slowed cancer cell growth was exhibited in the NK+IL-2-administered group, the Fc-IL21 monomer-administered group, and the Fc-IL21 dimer-administered group, and most of all, the Fc-IL21 monomer exhibited an excellent antitumor effect, as compared to the Fc-IL21 dimer. That is, it was confirmed that co-administration of an NK cellular therapeutic agent and the Fc-IL21 monomer to a xenograft skin cancer model (human A375 melanoma) enhanced the in vivo anticancer function of NK cells.

Figure 12B:
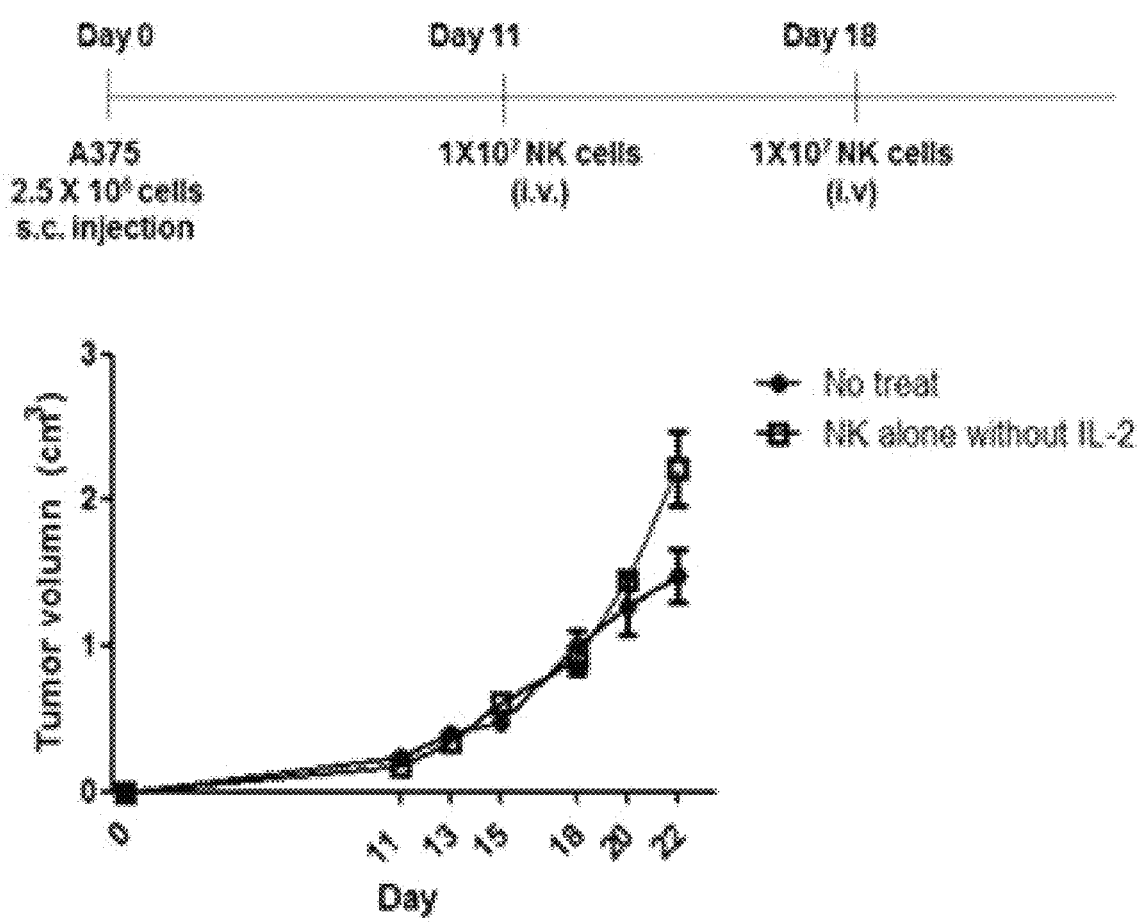
FIG. 12B illustrates results showing the size of tumor upon treatment with NK cells only in the xenograft human melanoma cancer cell.

In addition, when IL-2 was not administered, human NK cells did not exhibit anticancer activity (see FIG. 12B). From these results, it was confirmed that it was necessary to co-administer IL-2 to observe an in vivo antitumor effect of NK cells.

INDUSTRIAL APPLICABILITY

A heterodimeric Fc-fused protein according to the present invention mimics a naturally present form of IL-21 as a monomer as much as possible, and thus may maintain the activity of IL-21 present in nature. In addition, IL-21 as a monomer may have excellent activity as compared to water-soluble IL-21 or dimer IL-21 and may exhibit significantly extended half-life in the body.

In addition, a heterodimeric Fc-fused protein form according to the present invention enables the preparation of a monomeric heterodimeric Fc-fused protein without an optimized process such as an additional purification process.

While the present invention has been particularly shown and described with reference to specific embodiments thereof, it will be obvious to those skilled in the art that such specific embodiments are merely exemplary embodiments and are not intended to limit the scope of the present invention. Thus, the true scope of the present invention should be defined by the appended claims and equivalents thereto.

The invention claimed is:

1. A heterodimeric Fc-fused protein comprising first and second Fc regions of an immunoglobulin heavy chain constant region (Fc) pair and in which IL-21 is bound to only one of the N-terminus or the C-terminus of the first Fc region or the second Fc region,
   wherein CH3 domains of the first Fc region and the second Fc region have a mutation,
   wherein the mutation comprises one or more mutations selected from the following (1)-(5):
   (1) amino acid residue substitution at position K360 of the CH3 domain of the first Fc region;
   (2) amino acid residue substitution at position Q347 of the CH3 domain of the second Fc region;
   (3) amino acid residue substitution at position K409 of the CH3 domain of the first Fc region;
   (4) amino acid residue substitution at position F405 of the CH3 domain of the second Fc region; and
   (5) amino acid residue substitution at position D399 of the CH3 domain of the second Fc region,
   wherein amino acid residue numbers are in accordance with EU index.

2. The heterodimeric Fc-fused protein according to claim 1, wherein the IL-21 is bound to only the N-terminus of the first Fc region or the second Fc region.

3. The heterodimeric Fc-fused protein according to claim 1, wherein each of the first Fc region and the second Fc region is an Fc region of immunoglobulin selected from the group consisting of human IgG1, IgG2, IgG3, IgG4, IgM, IgA, IgD, and IgE.

4. The heterodimeric Fc-fused protein according to claim 1, wherein the first Fc region and the second Fc region are included as Fc regions obtained from an immunoglobulin selected from the group consisting of human IgG1, IgG2, IgG3, IgG4, IgM, IgA, IgD, and IgE.

5. The heterodimeric Fc-fused protein according to claim 1, wherein the mutation of the CH3 domain of the first Fc region or the second Fc region comprises one or more mutations selected from the following (1) (4):
   (1) K360E amino acid residue substitution at position K360 of the CH3 domain of the first Fc region;
   (2) Q347R amino acid residue substitution at position Q347 of the CH3 domain of the second Fc region;
   (3) K409W amino acid residue substitution at position K409 of the CH3 domain of the first Fc region; and
   (4) F405T amino acid residue substitution at position F405 of the CH3 domain of the second Fc region and D399V amino acid residue substitution at position D399 of the CH3 domain of the second Fc region,
   wherein amino acid residue numbers are in accordance with EU index.

6. A pharmaceutical composition comprising the heterodimeric Fc-fused protein according to claim 1 and a pharmaceutically acceptable carrier.

* * * * *

SEQUENCE LISTING

```
<160> NUMBER OF SEQ ID NOS: 7

<210> SEQ ID NO 1
<211> LENGTH: 107
<212> TYPE: PRT
<213> ORGANISM: Artificial Sequence
<220> FEATURE:
<223> OTHER INFORMATION: IgG4-EW

<400> SEQUENCE: 1

Gly Gln Pro Arg Glu Pro Gln Val Tyr Thr Leu Pro Pro Ser Gln Glu
1               5                   10                  15

Glu Met Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60
```

```
Phe Leu Tyr Ser Trp Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105
```

<210> SEQ ID NO 2
<211> LENGTH: 107
<212> TYPE: PRT
<213> ORGANISM: Artificial Sequence
<220> FEATURE:
<223> OTHER INFORMATION: IgG4-RVT

<400> SEQUENCE: 2

```
Gly Gln Pro Arg Glu Pro Arg Val Tyr Thr Leu Pro Pro Ser Gln Glu
 1               5                  10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Val Ser Asp Gly Ser Phe
 50                  55                  60

Thr Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105
```

<210> SEQ ID NO 3
<211> LENGTH: 131
<212> TYPE: PRT
<213> ORGANISM: Artificial Sequence
<220> FEATURE:
<223> OTHER INFORMATION: human IL21

<400> SEQUENCE: 3

```
Gln Asp Arg His Met Ile Arg Met Arg Gln Leu Ile Asp Ile Val Asp
 1               5                  10                  15

Gln Leu Lys Asn Tyr Val Asn Asp Leu Val Pro Glu Phe Leu Pro Ala
                20                  25                  30

Pro Glu Asp Val Glu Thr Asn Cys Glu Trp Ser Ala Phe Ser Cys Phe
             35                  40                  45

Gln Lys Ala Gln Leu Lys Ser Ala Asn Thr Gly Asn Asn Glu Arg Ile
 50                  55                  60

Ile Asn Val Ser Ile Lys Lys Leu Lys Arg Lys Pro Pro Ser Thr Asn
 65                  70                  75                  80

Ala Gly Arg Arg Gln Lys His Arg Leu Thr Cys Pro Ser Cys Asp Ser
                 85                  90                  95

Tyr Glu Lys Lys Pro Pro Lys Glu Phe Leu Glu Arg Phe Lys Ser Leu
            100                 105                 110

Leu Gln Lys Met Ile His Gln His Leu Ser Ser Arg Thr His Gly Ser
        115                 120                 125

Glu Asp Ser
        130
```

<210> SEQ ID NO 4

```
<211> LENGTH: 107
<212> TYPE: PRT
<213> ORGANISM: Artificial Sequence
<220> FEATURE:
<223> OTHER INFORMATION: IgG1 WT

<400> SEQUENCE: 4

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: IgG2 WT

<400> SEQUENCE: 5

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: IgG3 WT

<400> SEQUENCE: 6

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Met Glu Trp Glu Ser Ser Gly Gln Pro Glu
        35                  40                  45
```

```
Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 7
<211> LENGTH: 107
<212> TYPE: PRT
<213> ORGANISM: Artificial Sequence
<220> FEATURE:
<223> OTHER INFORMATION: IgG4 WT

<400> SEQUENCE: 7

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
                100                 105
```